United States Patent
Kobayashi

(10) Patent No.: US 10,485,518 B2
(45) Date of Patent: Nov. 26, 2019

(54) DIAGNOSTIC IMAGING APPARATUS, CONTROL METHOD, PROGRAM, AND COMPUTER-READABLE STORAGE MEDIUM

(71) Applicant: TERUMO KABUSHIKI KAISHA, Kanagawa (JP)

(72) Inventor: Youhei Kobayashi, Hadano (JP)

(73) Assignee: TERUMO KABUSHIKI KAISHA, Shibuya-ku, Tokyo (JP)

( * ) Notice: Subject to any disclaimer, the term of this patent is extended or adjusted under 35 U.S.C. 154(b) by 883 days.

(21) Appl. No.: 15/074,059

(22) Filed: Mar. 18, 2016

(65) Prior Publication Data

US 2016/0270766 A1 Sep. 22, 2016

(30) Foreign Application Priority Data

Mar. 20, 2015 (JP) .................. 2015-058261

(51) Int. Cl.
*A61B 5/00* (2006.01)
*A61B 8/08* (2006.01)
(Continued)

(52) U.S. Cl.
CPC .......... *A61B 8/5261* (2013.01); *A61B 5/0066* (2013.01); *A61B 5/743* (2013.01);
(Continued)

(58) Field of Classification Search
CPC ..... A61B 8/5261; A61B 5/743; A61B 5/0066; A61B 5/7425; A61B 8/54; A61B 8/0891; A61B 8/12; A61B 8/4418; A61B 8/463
See application file for complete search history.

(56) References Cited

U.S. PATENT DOCUMENTS 6,200,268 B1 3/2001 Vince et al.
7,935,060 B2 5/2011 Schmitt et al.
(Continued)

FOREIGN PATENT DOCUMENTS

JP 2004180932 A 7/2004
JP 2005-095624 A 4/2005
(Continued)

OTHER PUBLICATIONS

Notification of Reasons for Refusal dated Dec. 4, 2018 for Japanese Application No. 2015-058261 and English translation (7 pages).

*Primary Examiner* — Joel Lamprecht
(74) *Attorney, Agent, or Firm* — Buchanan Ingersoll & Rooney PC

(57) ABSTRACT

An imaging apparatus and method determines distribution and a type of tissue attribute in a vascular cross section based on reflected wave data of ultrasound detected by an imaging core and interference light data including a reflected wave of light detected by the imaging core. A portion of match/mismatch is determined by comparing respectively classified vascular tissue attributes. Then, the distribution of the body tissue attributes is displayed by superimposing the distribution on any one of an ultrasound cross-sectional image, an optical interference cross-sectional image, and a composite image between the ultrasound cross-sectional image and the optical interference cross-sectional image, in a display form in which the match/mismatch can be identified.

9 Claims, 9 Drawing Sheets

(51) Int. Cl.
*A61B 8/00* (2006.01)
*A61B 8/12* (2006.01)
*A61B 5/02* (2006.01)

(52) U.S. Cl.
CPC .......... *A61B 5/7425* (2013.01); *A61B 8/0891* (2013.01); *A61B 8/12* (2013.01); *A61B 8/4416* (2013.01); *A61B 8/463* (2013.01); *A61B 8/5223* (2013.01); *A61B 8/54* (2013.01); *A61B 5/02007* (2013.01); *A61B 8/445* (2013.01)

(56) References Cited

U.S. PATENT DOCUMENTS

| | | |
|---|---|---|
| 2005/0101859 A1 | 5/2005 | Maschke |
| 2006/0050943 A1 | 3/2006 | Ozaki |
| 2009/0306520 A1* | 12/2009 | Schmitt ................ A61B 5/0066 600/476 |
| 2011/0208017 A1 | 8/2011 | Kuban et al. |
| 2012/0083696 A1 | 4/2012 | Kitamura |
| 2013/0345556 A1 | 12/2013 | Courtney et al. |
| 2014/0180107 A1* | 6/2014 | Mai ...................... A61B 8/4461 600/445 |
| 2015/0005626 A1 | 1/2015 | Kaneko |

FOREIGN PATENT DOCUMENTS

| | | |
|---|---|---|
| JP | 3772002 B2 | 2/2006 |
| JP | 201011964 A | 1/2010 |
| JP | 2010-516304 A | 5/2010 |
| JP | 4933045 B2 | 2/2012 |
| JP | 201275702 A | 4/2012 |
| JP | 2014-097417 A | 5/2014 |
| WO | 2013145689 A1 | 10/2013 |

\* cited by examiner

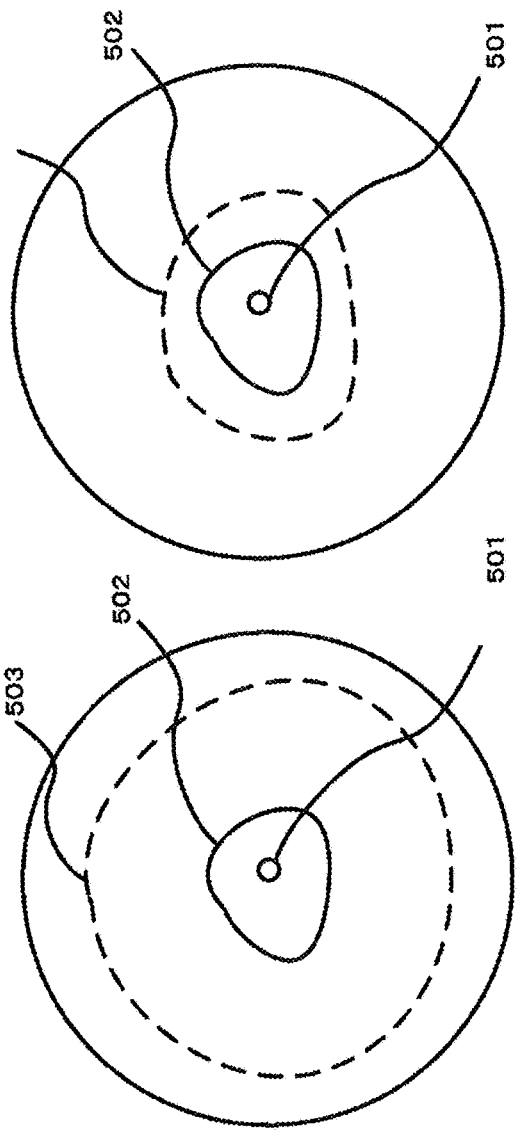

TISSUE ATTRIBUTE BASED ON
ULTRASOUND DATA

TISSUE ATTRIBUTE BASED ON
OPTICAL INTERFERENCE DATA

TISSUE ATTRIBUTE BASED ON
ULTRASOUND DATA
(AFTER CORRECTION)

TISSUE ATTRIBUTE BASED ON
ULTRASOUND DATA AND
OPTICAL INTERFERENCE DATA

| OCT / IVUS | CALCIFICATION PLAQUE | FIBROSIS PLAQUE | LIPID PLAQUE |
|---|---|---|---|
| CALCIFICATION PLAQUE | CALCIFICATION PLAQUE | — | — |
| FIBROSIS PLAQUE | — | FIBROSIS PLAQUE OR MACROPHAGE | — |
| LIPID PLAQUE | — | — | LIPID PLAQUE |

FIG. 9

DIAGNOSTIC IMAGING APPARATUS, CONTROL METHOD, PROGRAM, AND COMPUTER-READABLE STORAGE MEDIUM

CROSS-REFERENCES TO RELATED APPLICATIONS

This application claims priority to Japanese Application No. 2015-058261 filed on Mar. 20, 2015, the entire content of which is incorporated herein by reference.

TECHNICAL FIELD

The present disclosure relates to an imaging apparatus for diagnosis, a control method thereof, a program, and a computer-readable recording medium.

BACKGROUND DISCUSSION

Conventionally, an imaging apparatus for diagnosis has been widely used in order to perform diagnosis on arteriosclerosis, to perform preoperative diagnosis before endovascular therapy which uses a high-function catheter such as a balloon catheter or a stent, or to verify results after surgery. The imaging apparatus for diagnosis includes an intravascular ultrasound (IVUS) device, an optical coherence tomography (OCT) device, and the like, which have different respective characteristics. For example, ultrasound reaches a relatively deep location of body tissues, and so an IVUS cross-sectional image is conveniently used in diagnosing tissues at a relatively deep location. On the other hand, light does not have a comparable reachable distance to ultrasound, but can be used to acquire higher-resolution images. Accordingly, although an optical cross-sectional image allows diagnosis only for tissues at a relatively shallow location, the image obtained thereby will have much higher resolution compared to the ultrasound. For the above-described reasons, a technique is known in which both an IVUS function and an OCT function are provided so as to display a composite image by setting a light-reachable limit to a boundary in an optical cross-sectional image and by employing the optical cross-sectional image on the inside from the boundary and an ultrasound cross-sectional image on the outside from the boundary, for example, as disclosed in Japanese Patent No. 3772002, U.S. Pat. No. 7,935,060, JP-T-2010-516304, and JP-A-2005-095624.

In addition, with the utilization of such an imaging apparatus for diagnosis, it is also possible to understand attribute classification and distribution of vascular tissues. For example, JP-A-2014-97417 discloses a technique of analyzing data obtained through the OCT function so as to classify a vascular cross-sectional image into body regions of Calcification, Fibrosis, and Lipid. In addition, Japanese Patent No. 4933045 and U.S. Pat. No. 6,200,268 each disclose a technique of similarly classifying body tissues, based on data obtained through the IVUS function.

SUMMARY

As described above, attribute classification of body tissues has been performed based on information obtained by independent scanning using either ultrasound or light. Consequently, the attribute classification is obtained when viewed in one direction, and so the accuracy thereof cannot be evaluated. In addition, the body attributes can only be classified with respect to Calcification, Fibrosis, and Lipid.

The present disclosure aims to provide a technique of visually and clearly informing a user of accuracy in classifying vascular tissues. In addition, the present disclosure aims to provide a technique which enables more detailed classification of probabilities in tissue conditions.

In order to achieve the above-described object and other objects, the present disclosure describes an imaging apparatus for diagnosis which generates a vascular cross-sectional image based on ultrasound and a vascular cross-sectional image based on optical interference by applying a probe for rotatably and movably accommodating an imaging core having an ultrasound transceiver and an optical transceiver.

The imaging apparatus for diagnosis has first classification means for determining distribution and a type of tissue attribute in a vascular cross section, based on reflected wave data of ultrasound detected by the imaging core, second classification means for determining the distribution and the type of the tissue attribute in the vascular cross section, based on interference light data including a reflected wave of light detected by the imaging core, determination means for determining a portion of match/mismatch by comparing respective vascular tissue attributes classified by the first classification means and the second classification means, and display means for displaying the distribution of body tissue attributes determined by the determination means in a display form in which the match/mismatch can be identified.

According to the present disclosure, it is possible to visually and clearly inform a user of accuracy in classifying vascular tissues. In addition, according to another aspect of the disclosure, it is also possible to perform more detailed classification on probabilities in tissue conditions.

BRIEF DESCRIPTION OF THE DRAWINGS

FIG. 5(a) schematically illustrates an ultrasound cross-sectional image according to the embodiment.

FIG. 5(b) schematically illustrates an optical cross-sectional image according to the embodiment.

FIG. 9 illustrates a table for determining tissue attributes according to the embodiment.

DETAILED DESCRIPTION

Hereinafter, embodiments according to the present disclosure will be described in detail with reference to the accompanying drawings. Throughout the specification, the same numbered reference elements have the same configuration.

Figure 1:
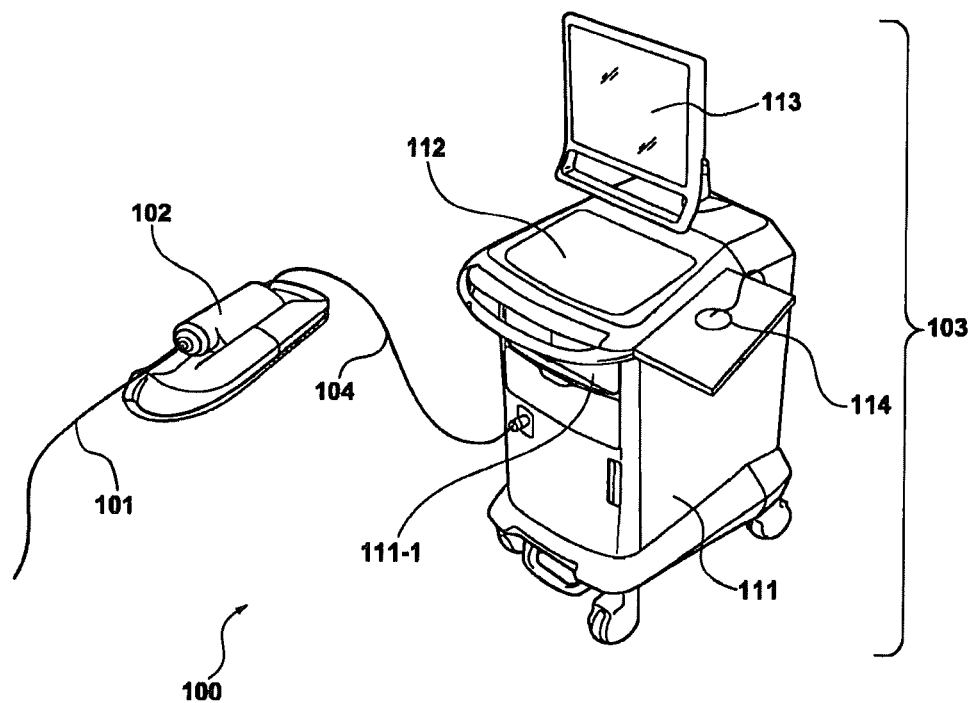
FIG. 1 illustrates an external configuration of an imaging apparatus for diagnosis according to an embodiment.

FIG. 1 illustrates an external configuration of an imaging apparatus for diagnosis 100 according to an embodiment. The imaging apparatus for diagnosis 100 has an IVUS function and an OCT function.

As illustrated in FIG. 1, the imaging apparatus for diagnosis 100 comprises a probe 101, a pullback unit 102, and an operation control device 103. The pullback unit 102 and the operation control device 103 are connected to each other via a connector 105 by a cable 104 for accommodating a signal line or an optical fiber.

The probe 101 is directly inserted into the blood vessel, and accommodates a rotatable imaging core which is movable in the longitudinal direction. An ultrasound transceiver which transmits ultrasound based on a pulse signal and receives a reflected wave from the inside of the blood vessel, and an optical transceiver which continuously transmits transmitted light (measurement light) into the blood vessel and continuously receives reflected light from the inside of the blood vessel are disposed in a distal end of the imaging core. The imaging apparatus for diagnosis 100 measures a state inside the blood vessel by applying the imaging core.

The probe 101 is detachably attached to the pullback unit 102. A motor incorporated in the pullback unit 102 is driven. In this manner, an operation in the axial direction and a rotation operation around the axis inside the blood vessel are regulated in the imaging core inside a catheter internally inserted into the probe 101. In addition, the pullback unit 102 functions as a relay device of a signal between the ultrasound transceiver and the optical transceiver inside the imaging core, and the operation control device 103. That is, the pullback unit 102 has a function to transmit an ultrasound drive signal output from the operation control device 103 to the ultrasound transceiver, and a function to transmit an electrical signal indicating a reflected wave from body tissues which is detected by the ultrasound transceiver to the operation control device 103. Then, the pullback unit 102 has a function to transmit measurement light output from the operation control device 103 to the optical transceiver, and has a function to transmit reflected light from body tissues which is detected by the optical transceiver to the operation control device 103.

When carrying out measurement, the operation control device 103 comprises a function for inputting various set values, and a function for displaying various blood vessel images after processing ultrasound data or optical interference data acquired by the measurement.

In the operation control device 103, a main body control unit 111 generates line data oriented in the radial direction from a rotation center position, based on a signal of the reflected wave of the ultrasound obtained by the measurement. Then, the main body control unit 111 generates an ultrasound cross-sectional image through an interpolation process of each line data. Furthermore, the main body control unit 111 generates interference light data by causing interference between the reflected light from the imaging core and the reference light obtained by separating the light from a light source. The main body control unit 111 generates the line data by performing FFT on the interference light data. Then, the main body control unit 111 generates a vascular cross-sectional image based on the optical interference through the interpolation process. The main body control unit 111 is embodied, for example, by a CPU executing a software program which is stored on a tangible, non-transitory computer-readable storage medium.

A printer and DVD recorder 111-1 prints a processing result in the main body control unit 111, or stores the processing result as data. A user inputs various set values and instructions via the operation panel 112. A monitor 113 (for example, LCD) serves as a display device, and displays various cross-sectional images generated in the main body control unit 111. A mouse 114 serves as a pointing device (coordinate input device).

Figure 2:
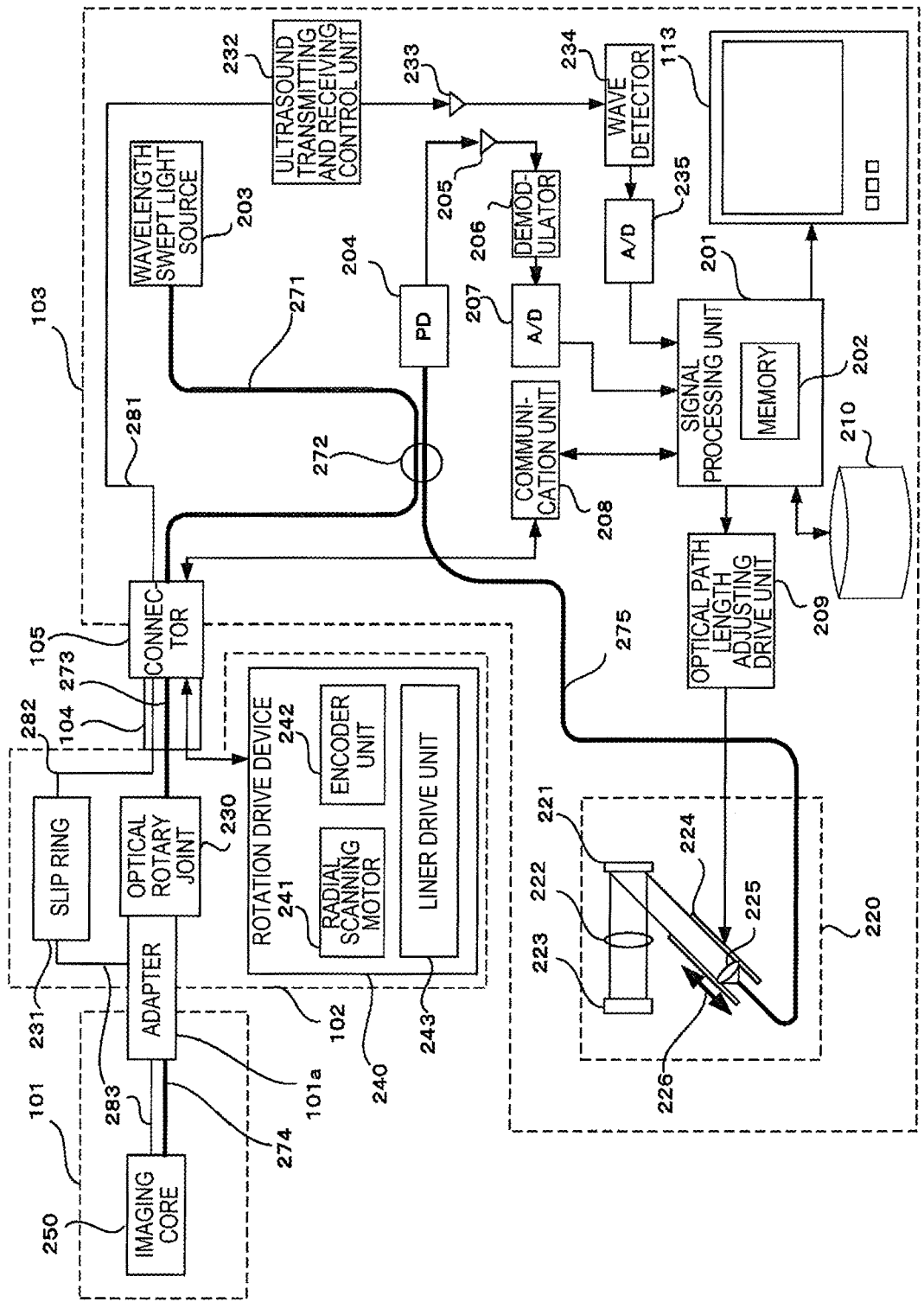
FIG. 2 is a block configuration diagram of the imaging apparatus for diagnosis according to the embodiment.

Next, a functional configuration of the imaging apparatus for diagnosis 100 will be described. FIG. 2 is a block configuration diagram of the imaging apparatus for diagnosis 100. Hereinafter referring to the drawing, a functional configuration of swept source OCT will be described.

In the drawing, the reference numeral 201 represents a signal processing unit for performing overall control on the imaging apparatus for diagnosis, and is configured to include several circuits together with a microprocessor. The reference numeral 210 is a non-volatile storage device represented by a hard disk, and stores various programs or data files executed by the signal processing unit 201. The reference numeral 202 represents a memory (RAM) disposed inside the signal processing unit 201. The reference numeral 203 represents a wavelength swept light source, and is a light source which repeatedly generates light having a wavelength varying along the time axis within a preset range.

The light output from the wavelength swept light source 203 is incident on one end of a first single mode fiber 271, and is transmitted toward the distal side. The first single mode fiber 271 is optically coupled to a fourth single mode fiber 275 in an optical fiber coupler 272 located in the middle.

The light which is incident on the first single mode fiber 271 and emitted toward the distal side from the optical fiber coupler 272 is guided to a second single mode fiber 273 via the connector 105. The other end of the second single mode fiber 273 is connected to an optical rotary joint 230 inside the pullback unit 102.

On the other hand, the probe 101 has an adapter 101*a* for being connected to the pullback unit 102. Then, the probe 101 is connected to the pullback unit 102 by the adapter 101*a*, thereby stably holding the probe 101 in the pullback unit 102. Furthermore, an end portion of a third single mode fiber 274 rotatably accommodated inside the probe 101 is connected to the optical rotary joint 230. As a result, the second single mode fiber 273 and the third single mode fiber 274 are optically coupled to each other. An imaging core 250 equipped with the optical transceiver (details to be described later with reference to FIG. 3) configured to include a mirror and a lens which emit light in a direction substantially straight with regard to the rotation axis is disposed in the other end (distal side of the probe 101) of the third single mode fiber 274.

As a result of the above-described configuration, the light emitted by the wavelength swept light source 203 is guided to the imaging core 250 disposed in an end portion of the third single mode fiber 274, via the first single mode fiber 271, the second single mode fiber 273, and the third single mode fiber 274. The optical transceiver of the imaging core 250 emits the light in a direction straight with regard to the axis of the fiber, and receives the reflected light. The received reflected light is reversely guided this time, and is caused to return to the operation control device 103.

On the other hand, an optical path length adjustment mechanism 220 performing fine adjustment on the optical path length of the reference light is disposed in an end portion opposite to the fourth single mode fiber 275 coupled to the optical fiber coupler 272. The optical path length adjustment mechanism 220 functions as optical path length changing means for changing the optical path length corresponding to variations in the length so that the variations in the length of the respective probes 101 can be absorbed, for example, in case where the probe 101 is replaced. Therefore, a collimator lens 225 positioned in one end portion of the fourth single mode fiber 275 is disposed on a single axis stage 224 which is movable as illustrated by an arrow 226 in the optical axis direction.

Specifically, in case where the probe 101 is replaced, the single axis stage 224 functions as optical path length changing means having a variable range of the optical path length which can absorb the variations in the optical path length of the probe 101. Furthermore, the single axis stage 224 also comprises a function as adjustment means for adjusting an offset. For example, even in case where the distal end of the probe 101 is not in close contact with a surface of body tissues, the optical path length is finely adjusted by the single axis stage. In this manner, it is possible to set a state of interfering with the reflected light from a surface position of the body tissues.

The optical path length of the single axis stage 224 is finely adjusted, and the light reflected on a mirror 223 via a grating 221 and a lens 222 is guided again to the fourth single mode fiber 275. In the optical fiber coupler 272, the light is mixed with light obtained from the second single mode fiber 273 side, and is received by a photodiode 204 as interference light.

The interference light received by the photodiode 204 in this way is subjected to photoelectric conversion, and is input to a demodulator 206 after being amplified by an amplifier 205. The demodulator 206 performs demodulation processing for extracting only a signal portion of the interfered light, and the output is input to an A/D converter 207 as an interference light signal.

The A/D converter 207 performs sampling in which the interference light signal is converted into 2,048 points at 90 MHz, for example, and generates digital data (interference light data) of one line. The reason for setting the sampling frequency to 90 MHz is on the assumption that approximately 90% of the wavelength swept cycle (25 μsec) is extracted as digital data of 2,048 points in case where the wavelength swept repetition frequency is set to 40 kHz. The sampling frequency is not particularly limited thereto.

The interference light data in a line unit which is generated by the A/D converter 207 is input to the signal processing unit 201, and is temporarily stored in the memory 202. Then, the signal processing unit 201 performs frequency resolution on the interference light data by means of FFT so as to generate data (line data) in the depth direction. The signal processing unit 201 builds an optical cross-sectional image at each position inside the blood vessel, based on the line data. In some cases, the signal processing unit 201 outputs the optical cross-sectional image to a monitor 113 at a predetermined frame rate.

The signal processing unit 201 is further connected to an optical path length adjusting drive unit 209 and a communication unit 208. The signal processing unit 201 performs control (optical path length control) on a position of the single axis stage 224 via the optical path length adjusting drive unit 209.

The communication unit 208 has several drive circuits incorporated therein, and communicates with the pullback unit 102 under the control of the signal processing unit 201. Specifically, the optical rotary joint inside the pullback unit 102 supplies a drive signal to a radial scanning motor so as to rotate the third single mode fiber, receives a signal from an encoder unit 242 so as to detect the rotation position of the radial motor, and supplies a drive signal to a linear drive unit 243 so as to pull the third single mode fiber 274 at a predetermined speed.

The above-described process in the signal processing unit 201 is realized in such a way that a computer is caused to execute the process by a predetermined program.

In the above-described configuration, if the probe 101 is located at a position of the diagnosis-targeted blood vessel (coronary artery or the like) of a patient, a transparent flash liquid is moved toward the distal end of the probe 101 by a user's operation so as to be discharged into the blood vessel through a guiding catheter or the like. This configuration is adopted in order to exclude the influence of the blood. Then, if the user inputs an instruction to start scanning, the signal processing unit 201 drives the wavelength swept light source 203 so as to drive the radial scanning motor 241 and the linear drive unit 243 (hereinafter, a light emitting and receiving process performed by driving the radial scanning motor 241 and the linear drive unit 243 is referred to as scanning). As a result, the wavelength swept light from the wavelength swept light source 203 is supplied to the imaging core 250 through the above-described route. In this case, the imaging core 250 located at the distal position of the probe 101 moves along the rotation axis while rotating. Accordingly, the imaging core 250 emits the light to a vascular lumen surface and receives the reflected light while rotating and moving along the vascular axis.

Figure 4:
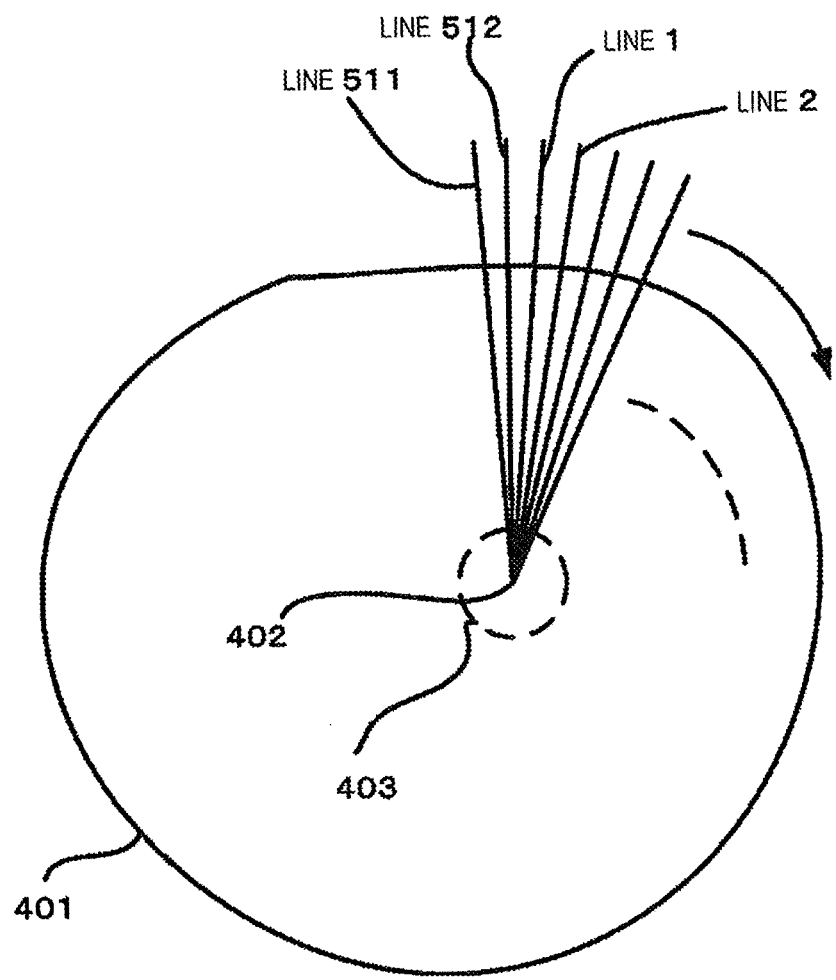
FIG. 4 illustrates a process of generating a cross-sectional image.

Here, a process relating to the generation of one optical cross-sectional image will be briefly described with reference to FIG. 4. The drawing is used in order to describe a reconfiguration process of a cross-sectional image of a vascular lumen surface 401 on which the imaging core 250 is located. While the imaging core 250 rotates once ($2\pi$=360 degrees), the measurement light is transmitted and received multiple times. If the light is transmitted and received once, it is possible to obtain data of one line in the light emitting direction. If FFT is performed on the data, line data indicating the reflection intensity (or absorption amount) of the light at each position oriented in the radial direction from the rotation center position can be obtained. Therefore, for example, if the light is transmitted and received 512 times during one rotation, it is possible to obtain 512 line data items radially extending from a rotation center 402. The 512 line data items become dense in the vicinity of the rotation center position, and become isolated from each other as the line data items are located further away from the rotation center position. Therefore, a pixel in an empty space between the respective lines is generated by performing known interpolation processing, thereby generating two-dimensional cross-sectional images which are visible to humans. Then, the generated two-dimensional cross-sectional images are connected to each other along the vascular axis. In this manner, it is possible to obtain a three-dimensional vascular image. It should be noted that the center position of the two-dimensional cross-sectional image coincides with the rotation center position of the imaging core 250, but is not the center position of the vascular cross section. In addition, although the light is weak, the light is reflected on a lens surface of the imaging core 250, a surface of a catheter, or the like. Accordingly, as illustrated by the reference numeral 403 in the drawing, several concentric circles with respect to the rotation center axis are generated.

Next, a configuration relating to image forming by applying ultrasound and process content will be described.

Scanning by applying the ultrasound is performed concurrently with the above-described optical interference scanning. That is, when the scanning is performed and the probe 101 is moved into the catheter sheath while the imaging core 250 is rotated, the ultrasound transceiver accommodated in the imaging core 250 emits the ultrasound, and detects the reflected wave. Therefore, it is necessary to generate and receive an electrical drive signal for driving the ultrasound transceiver accommodated in the imaging core 250, and to receive an ultrasound detection signal output from the ultrasound receiver. An ultrasound transmitting and receiving control unit 232 transmits the drive signal, and receives the detected signal. The ultrasound transmitting and receiving control unit 232 and the imaging core 250 are connected to each other via signal line cables 281, 282, and 283. Since the imaging core 250 rotates, the signal line cables 282 and 283 are electrically connected to each other via a slip ring 231 disposed inside the pullback unit 102. Illustration is made so that the signal line cables 281 to 283 are connected to each other by using a single line, but multiple signal lines are actually accommodated therein.

The ultrasound transmitting and receiving control unit 232 is operated under the control of the signal processing unit 201, drives the ultrasound transceiver accommodated in the imaging core 250, and generates an ultrasound pulse wave. The ultrasound transceiver converts the reflected wave from vascular tissues into an electrical signal, and supplies the electrical signal to the ultrasound transmitting and receiving control unit 232. The ultrasound transmitting and receiving control unit 232 outputs the received ultrasound signal to an amplifier 233 so as to be amplified. Thereafter, the amplified ultrasound signal is supplied to the signal processing unit 201 as ultrasound data through a wave detector 234 and an A/D converter 235, and is temporarily stored in the memory 202. The A/D converter 235 performs sampling in which the ultrasound signal output from a wave detector 454 is converted into 200 points at 30.6 MHz, and generates digital data (ultrasound data) of one line. Here, the sampling frequency is set to 30.6 MHz, but is calculated on the assumption that 200 point sampling is performed on the depth of 5 mm when a sound speed is set to 1,530 m/sec. Therefore, the sampling frequency is not particularly limited thereto.

The signal processing unit 201 generates line data corresponding to the gray scale, based on the ultrasound data stored in the memory 202. Thereafter, similarly to the reconfiguration process of the optical cross-sectional image, each line data item is arranged in a two-dimensional manner, and is subjected to interpolation. In this manner, an ultrasound cross-sectional image is generated at each position inside the blood vessel.

Next, a structure of the imaging core 250 in the probe 101 will be described with reference to FIG. 3.

Figure 3:
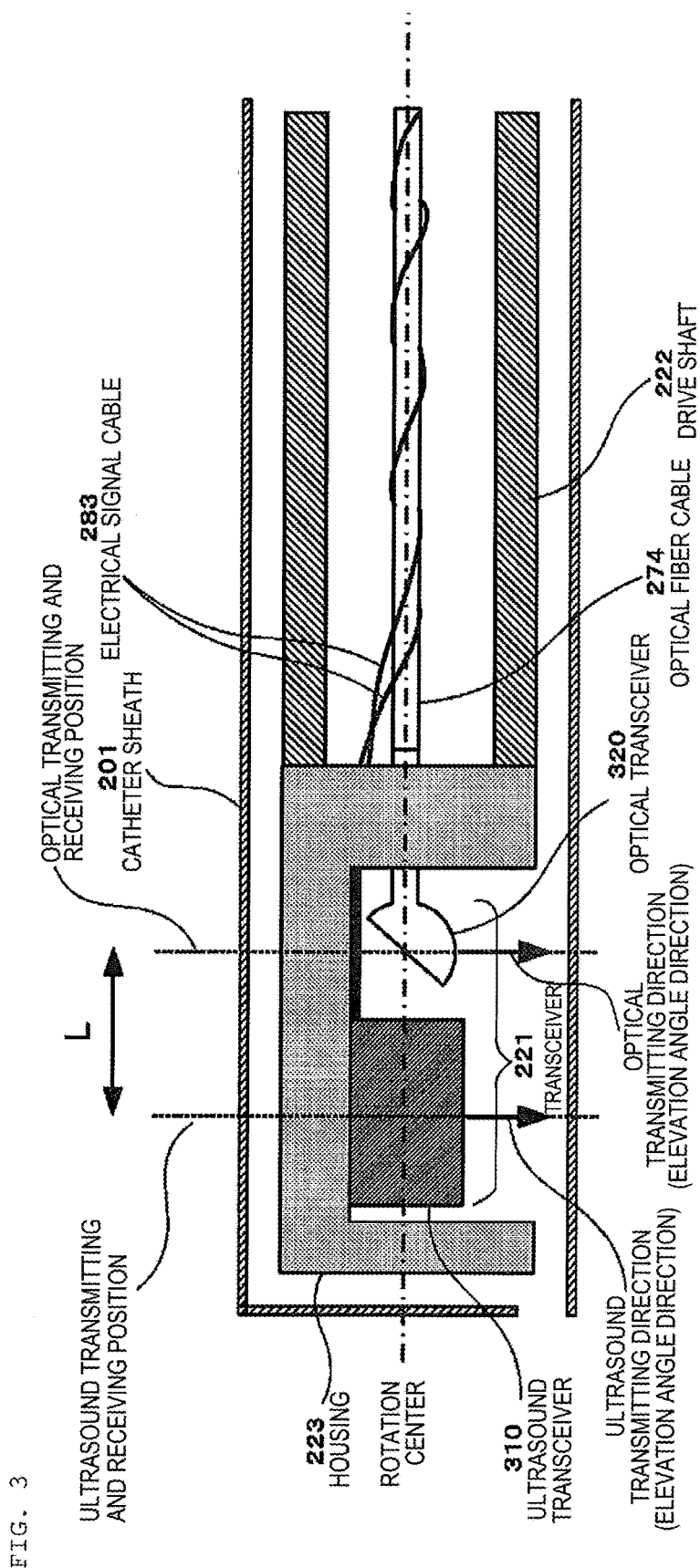
FIG. 3 illustrates a cross-sectional configuration of an imaging core and an arrangement of an ultrasound transceiver and an optical transceiver.

FIG. 3 illustrates a cross-sectional image of the distal portion of the probe 101. The distal portion of the probe 101 is configured to include a transparent catheter sheath 201 in order to allow the light to pass therethrough. As illustrated in the drawing, a transceiver 221 arranged inside the housing 223 comprises an ultrasound transceiver 310 and an optical transceiver 320. The ultrasound transceiver 310 and the optical transceiver 320 are arranged by leaving a distance L therebetween along the axial direction on the rotation center axis (on a one-dot chain line in the drawing) of a drive shaft 222. As illustrated, the optical transceiver 320 is configured to include a hemispherical ball lens disposed in the end portion of the third single mode fiber 274. According to this configuration, an inclined surface thereof enables the light incident from the third single mode fiber 274 to be transmitted toward vascular tissues after being reflected in the illustrated arrow direction, and enables the reflected light from the vascular tissues to be transmitted toward the third single mode fiber 274.

In this configuration, the ultrasound transceiver 310 is arranged on the distal side of the probe 101, and the optical transceiver 320 is arranged on the proximal side of the probe 101.

In addition, the ultrasound transceiver 310 and the optical transceiver 320 are attached to the inside of the housing 223 so that the ultrasound transmitting direction (elevation angle direction) of the ultrasound transceiver 310 and the light transmitting direction (elevation angle direction) of the optical transceiver 320 are respectively approximately 90° with respect to the axial direction of the drive shaft 222. The attachment may be performed by slightly shifting the respective transmitting directions from 90° so as not to receive the reflection on a surface inside the lumen of the catheter sheath 201 in the probe 101.

The signal line cable 283 connected to the ultrasound transceiver 310 and the third single mode fiber 274 connected to the optical transceiver 320 are accommodated inside the drive shaft 222. The signal line cable 283 is wound around the third single mode fiber 274 in a spiral shape.

As illustrated in FIG. 3, the ultrasound transceiver 310 and the optical transceiver 320 are arranged by leaving a distance L therebetween along the axis. Therefore, an offset based on the distance L, a rotation speed w of the imaging core 250, and a moving speed v along the rotation axis is present between the ultrasound line data and the optical interference data which are obtained at the same timing.

Therefore, the offset is applied, when the ultrasound cross-sectional image and the optical cross-sectional image are generated at the same location in the blood vessel.

Hitherto, a basic configuration and function of the imaging apparatus for diagnosis according to the embodiment has been described. Next, a characteristic point of the embodiment will be described.

As discussed above, there are known methods in which a tissue attribute region can be classified into the calcification plaque, the fibrosis plaque, the lipid plaque, and the like by analyzing the optical interference data and the ultrasound data which are obtained through the scanning process. Then, according to the embodiment, the probe 101 utilized by the imaging apparatus for diagnosis has the imaging core 250 which accommodates both the ultrasound transceiver 310 and the optical transceiver 320. Therefore, if the data obtained through each scanning is analyzed, it is possible to classify the tissue attribute region for each of the ultrasound cross-sectional image and the optical cross-sectional image at the same location in the blood vessel. In this regard, the operation control device 103, in processing the ultrasound data and optical interference data acquired by the measurement according to these known methods, corresponds to an example of first classification means for determining distribution and a type of tissue attribute in a vascular cross section, based on reflected wave data of ultrasound detected by the imaging core, and second classification means for determining the distribution and the type of the tissue attribute in the vascular cross section, based on interference light data including a reflected wave of light detected by the imaging core.

According to the embodiment, both classification results are compared with each other, and a user is informed of the fact that regions mutually having the same tissue attribute can be classified more accurately than a region having the tissue attribute detected by an apparatus having a single transceiver. On the other hand, in case where the same region is classified into different tissue attributes, the user is informed of the fact that any one or both are inaccurately classified. Then, in case where the region is in a specific relationship, the user is informed of a possibility that the region cannot be estimated by the classification performed so far. Hereinafter, a process for realizing the related point will be described.

The blood vessel has a triple-layer structure of the intima, tunica media, and tunica adventitia, from the inside through which the blood vessel flows. FIG. 5(a) schematically illustrates an ultrasound cross-sectional image of the blood vessel. The reference numeral 501 in the drawing corresponds to the catheter sheath (reference numeral 403 in FIG. 4), and the center represents a rotation center position of the imaging core. The reference numeral 502 represents a vascular lumen surface (surface of the intima) which is in contact with the blood. The reference numeral 503 represents the external elastic lamina located at the boundary between the tunica media and the tunica adventitia. The ultrasound reaches the tunica adventitia on the outer side further from the external elastic lamina. Accordingly, an ultrasound cross-sectional image includes the tunica adventitia. If the classification of tissue attributes obtained by analyzing ultrasound data is performed on the inner side further from the external elastic lamina, it is possible to estimate that the classification is accurate to some degree. With regard to a position of the external elastic lamina, a candidate position thereof can be determined by radially searching for an ultrasound line from the rotation center position of the imaging core and finding out a position where brightness thereof rapidly increases. However, if single line data is used, there is a possibility that many related candidate locations are present. However, if the adjacent line data is also sequentially used, one continuous circumference can be identified. Thus, the external elastic lamina can be identified.

On the other hand, light does not reach as deeply as the ultrasound reaches. FIG. 5(b) schematically illustrates an optical cross-sectional image. The reference numerals 501 and 502 in FIG. 5(b) are the same as those in FIG. 5(a). As illustrated in FIG. 5(b), the light reaches a portion which is relatively shallow from the lumen surface. The reference numeral 504 in the drawing represents a light-reachable boundary. In case of optical interference data, the light does not reach the outer side beyond the light-reachable boundary 504 (to be more precise, since reflected light cannot be detected at the position). Accordingly, the outer side further from the light-reachable boundary 504 generally shows as black monochrome in an optical cross-sectional image. Therefore, a position of a light-reachable depth limit is radially searched for from the rotation center position of the imaging core, and a location where brightness thereof rapidly decreases and thereafter gently decreases is found. In this manner, a position where the brightness rapidly decreases immediately before the brightness gently decreases is determined as a candidate position. For this reason, a target region for which classification of tissue attributes based on optical interference data is performed is a region within the light-reachable boundary 504.

For the above-described reason, in the embodiment, the following classification process is performed in order to classify attributes of vascular tissues by applying both the ultrasound and the light.

(i) On the outer side of the light-reachable boundary, it is estimated that the classification of the tissue attributes based on the ultrasound data is correct.

(ii) On the inner side of the light-reachable boundary, the classification is estimated by utilizing the tissue attributes which are respectively obtained from the ultrasound data and the optical interference data.

The above-described (i) does not need further description. Therefore, hereinafter, the latter (ii) will be further studied in detail.

In case of (ii), two cases can theoretically occur such as a case where the same attribute is shown at the same region in case where the attributes are obtained from both the ultrasound data and the optical interference data and a case where the same attribute is not shown. Regions in which the tissue attributes obtained by analyzing the ultrasound data and the optical interference data are distributed are not always have the same size and the same shape. Therefore, if a common part of both the sizes and both the shapes is equal to or greater than a predetermined threshold value (for example, 90%) of each area, the regions are estimated as regions having the same tissue attribute as each other. In addition, in case where one is completely included in the other, a region corresponding to the included one side is estimated as a region having the same tissue attribute as each other.

FIG. 9 illustrates a table for determining tissue attributes in case where both the ultrasound data and the optical interference data according to the embodiment are applied.

"IVUS" represents the ultrasound data, and "OCT" represents the optical interference data. According to the embodiment, in any one of the ultrasound data and the optical interference data, the tissue attributes are classified into three types of the calcification plaque, the fibrosis plaque, and the lipid plaque. Therefore, a combination thereof is as illustrated in FIG. 9. In addition, the illustrated mark "-" represents that the attribute is inaccurate (or unclear). In addition, if a macrophage is present in case where the tissue attribute is determined as the fibrosis plaque by analyzing the ultrasound data and the optical interference data, the specific case satisfies the following condition.

"In case where with respect to a region having the tissue attribute which is determined as the fibrosis plaque by analyzing the ultrasound data, the inner side (side through which the blood flows) of the region is determined as the fibrosis plaque and the outer side is determined as the lipid plaque, the inner side region is estimated as the macrophage."

Figure 6A:
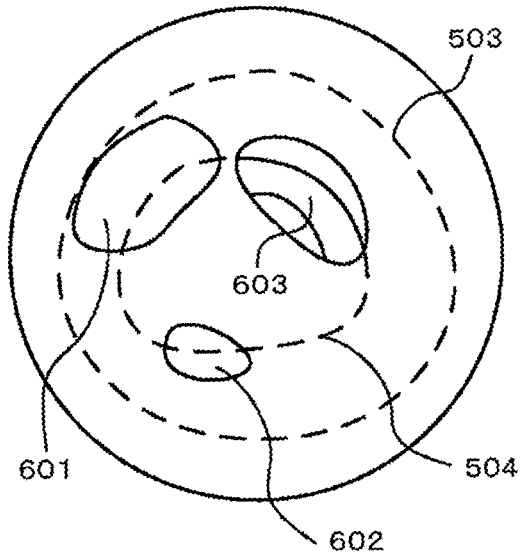
FIG. 6(a) is a view of tissue attribute regions based on ultrasound data for describing a classification process of vascular tissues according to the embodiment.
Figure 6B:
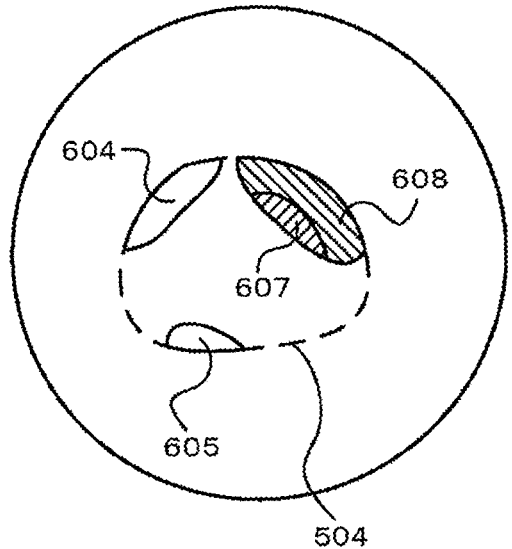
FIG. 6(b) is a view of tissue attribute regions based on optical interference data for describing a classification process of vascular tissues according to the embodiment.
Figure 6C:
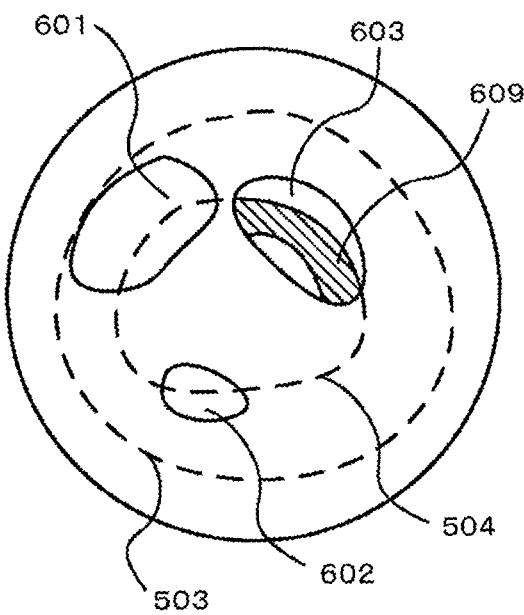
FIG. 6(c) is a view of tissue attribute regions based on ultrasound data after correction for describing a classification process of vascular tissues according to the embodiment.
Figure 6D:
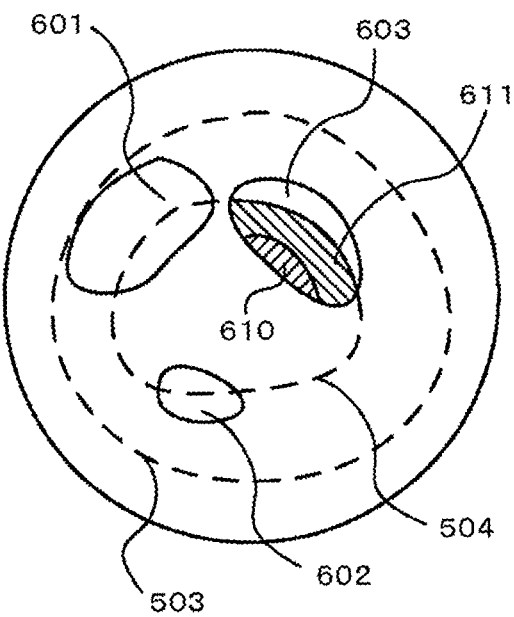
FIG. 6(d) is a view of tissue attribute regions based on ultrasound data and optical interference data for describing a classification process of vascular tissues according to the embodiment.

In view of the above-described condition, the ultrasound data and the optical interference data are now analyzed and the tissue attribute regions are determined as illustrated in FIGS. 6(a) and 6(b). FIG. 6(a) illustrates tissue attribute regions 601 to 603 based on the ultrasound data. The regions 601 and 602 are determined as the calcification plaque, and the region 603 is determined as the fibrosis plaque. FIG. 6(b) illustrates tissue attribute regions 604 to 607 based on the optical interference data. The regions 604 and 605 are determined as the calcification plaque, the region 607 is determined as the fibrosis plaque, and a region 608 is determined as the lipid plaque.

As illustrated, the region 601 includes the region 604. Then, a region on the inner side further from the light-reachable boundary in the region 601 and a common area ratio with the region 604 are mutually beyond a threshold value, and both the regions are determined as the same tissue attribute. Accordingly, it is estimated that the tissue attributes in the regions 601 and 604 are correctly determined. For the same reason, a region on the inner side further from the light-reachable boundary in the region 602 and a common area ratio with the region 605 are mutually beyond a threshold value, and both the regions are determined as the same tissue attribute. Accordingly, it is estimated that the tissue attributes are also correctly determined.

On the other hand, the region 603 completely includes the regions 607 and 608. However, whereas the region on the inner side further from the light-reachable boundary in the region 603 is determined as the fibrosis plaque, the region 608 is determined as the lipid plaque. In this way, different determination results are obtained from the ultrasound data and the optical interference data. Therefore, there is a possibility that a region on the inner side further from the light-reachable boundary in the region 603, and the regions 608 and 607 may be determined as inaccurate or may be erroneously determined. The point will be further described in detail. Furthermore, when estimating that the above-discussed tissue attributes are either correctly determined or inaccurate or erroneously determined, the operation control device 103 corresponds to an example of determination means for determining a portion of match/mismatch by comparing respective vascular tissue attributes classified by the first classification means and the second classification means.

According to the embodiment, as a background image for display, any image can be designated from an ultrasound cross-sectional image, an optical cross-sectional image, and a composite image between the ultrasound cross-sectional image and the optical cross-sectional image. The operation panel 112, when being used to designate an image as the background image, corresponds to an example of first selection means for selecting any one of the ultrasound cross-sectional image, the optical interference cross-sectional image, and the composite image between the ultrasound image and the optical tomographic image, as the background image displayed by the display means.

Furthermore, as the tissue attribute to be displayed by being superimposed on the cross-sectional image, the tissue attribute can be designated from the following three tissue attributes. The operation panel 112, when being used to designate a tissue attribute to be superimposed on the cross-sectional image, corresponds to an example of second selection means for selecting any one for display, as the tissue attributes displayed by the display means, among the tissue attributes obtained from reflected wave data of ultrasound, the tissue attributes obtained from interference light data, and tissue attribute information based on both the ultrasound reflected wave data and the interference light data.

(1) Tissue attribute based on the ultrasound data.
(2) Tissue attribute based on the optical interference data
(3) Tissue attribute based on both the ultrasound data and the optical interference data According to the embodiment, in case where the above-described (1) is selected, the tissue attribute illustrated in FIG. 6(*c*) is displayed. In this case, the regions 601 and 602 are determined as the calcification plaque, and the determination is the same as the determination using the optical interference data. Accordingly, the determination is displayed as accurate. Then, the region 603 is determined as the fibrosis plaque, and the determination is displayed as accurate. However, a region 609 included therein (corresponding to the region 608 in FIG. 6(*b*)) is displayed so that the determination as the fibrosis plaque is inaccurate. The display device 113, when displaying the tissue attribute illustrated in FIG. 6(*c*), corresponds to an example of display means for displaying the distribution of body tissue attributes determined by the determination means in a display form in which the match/mismatch can be identified.

Types of tissue attributes can be distinguished from each other by using a boundary or a color inside the boundary. Whether the determination is accurate or inaccurate is displayed depending on whether the color brightness is high or low. As a result of the above-described configuration, in case where the tissue attribute based on the ultrasound data is displayed, it is possible to identify that each region has any tissue attribute, and to further identify whether the determination is accurate or inaccurate. The point is the same as that in the following description.

According to the embodiment, in case where (2) is selected, the tissue attribute illustrated in FIG. 6(*b*) is displayed. In this case, the regions 604 and 605 are determined as the calcification plaque, and the determination is the same as the determination using the ultrasound data. Accordingly, the determination is displayed as accurate. In addition, the region 608 is determined as the lipid plaque based on the optical interference data, and the determination result is inconsistent with the determination result based on the ultrasound data. Accordingly, the determination is displayed as inaccurate. In the region 607, the determination result is inconsistent with the determination result based on the ultrasound data. Accordingly, the determination is displayed as accurate. In view of the following description (3), with regard to a display form of the region 607, the determination may be displayed as inaccurate.

According to the embodiment, in case where (3) is selected, the tissue attribute illustrated in FIG. 6(*d*) is displayed. A region range displayed by the ultrasound cross-sectional image is wider than that displayed by the optical cross-sectional image. Accordingly, the tissue attribute serving as a base is the tissue attribute based on the ultrasound data. Then, the regions 604 and 605 are respectively and completely included in the regions 601 and 602, and have the same tissue attribute. Therefore, the regions 601 and 602 are displayed as the calcification plaque, and are displayed as accurate. On the other hand, except for the regions 610 and 611, the region 603 is present outside the light-reachable boundary. Accordingly, the region 603 is displayed as the fibrosis plaque, and is displayed as accurate.

Then, the regions 610 and 611 match the previously described condition. That is, the region 603 including the regions 610 and 611 is classified as the fibrosis plaque through the determination process of the tissue attributes based on the ultrasound data. Then, in the regions 610 and 611, the region 610 is close to the rotation position of the imaging core. Accordingly, the region 610 is present on the side (inner side) through which the blood flows, and the region 611 is located on the outer side. Then, through the determination process of the tissue attributes based on the optical interference data, the region 610 is determined as the fibrosis plaque, and the region 611 is determined as the lipid plaque. Therefore, the region 610 is estimated as the microphage. Then, the region 611 is displayed as the lipid plaque, and the tissue attributes based on the ultrasound data and the optical interference data are different from each other. Accordingly, the determination is displayed as inaccurate. The macrophage represents the tissue attributes determined by utilizing both data for the first time. Accordingly, the macrophage may be displayed in a color different from that of other tissue attributes, and does not represent whether the determination is accurate or inaccurate. FIG. 9 illustrates the reason that the tissue attribute can become the macrophage in case where the fibrosis plaque is determined by utilizing the ultrasound data and the fibrosis plaque is determined by utilizing the optical interference data.

When (3) is selected, even in case where the same region is determined as the lipid plaque by utilizing the ultrasound data and is determined as the calcification plaque by utilizing the optical interference data, the mark "-" is displayed on the table in FIG. 9. Accordingly, the corresponding region is basically displayed in a color indicating "unclear". However, the tissue attribute determined as accurate may be displayed on the location of the mark "-". In case of this combination, the analysis result of the optical interference data which clearly shows a boundary between the calcification plaque and the surrounding tissue is considered as accurate. Accordingly, as the accurate determination result, the calcification plaque is displayed. In actual practice, a database is built in advance by using the determination results which are considered more accurate. Based on the database, the determination is displayed by providing classification of the accurate determination results. In this case, the database is stored in a hard disk 210 or the memory 202. The display device 113, when displaying the tissue attribute illustrated in FIG. 6(d), corresponds to an example of display means for displaying a classification of the tissue attributes determined based on a result of the determination means and a predetermined database.

A configuration may be adopted in which preferentially utilizing either the tissue attribute based on the ultrasound data or the tissue attribute based on the optical interference data can be designated. In this case, preferentially to analyze the ultrasound data is designated. In case where the same region is determined as the lipid plaque by using the ultrasound data and is determined as the calcification plaque by using the optical interference data, the region corresponding to the inaccurate determination is displayed as the lipid plaque.

As described above, even in case where the tissue attribute based on only the ultrasound data or only the optical interference data is displayed, the accurate classification together with the inaccurate classification can be displayed. Furthermore, in case where the tissue attribute is displayed by applying both the ultrasound data and the optical interference data, it is also possible to display not only the accuracy but also a possibility of a new tissue attribute.

Figure 7:
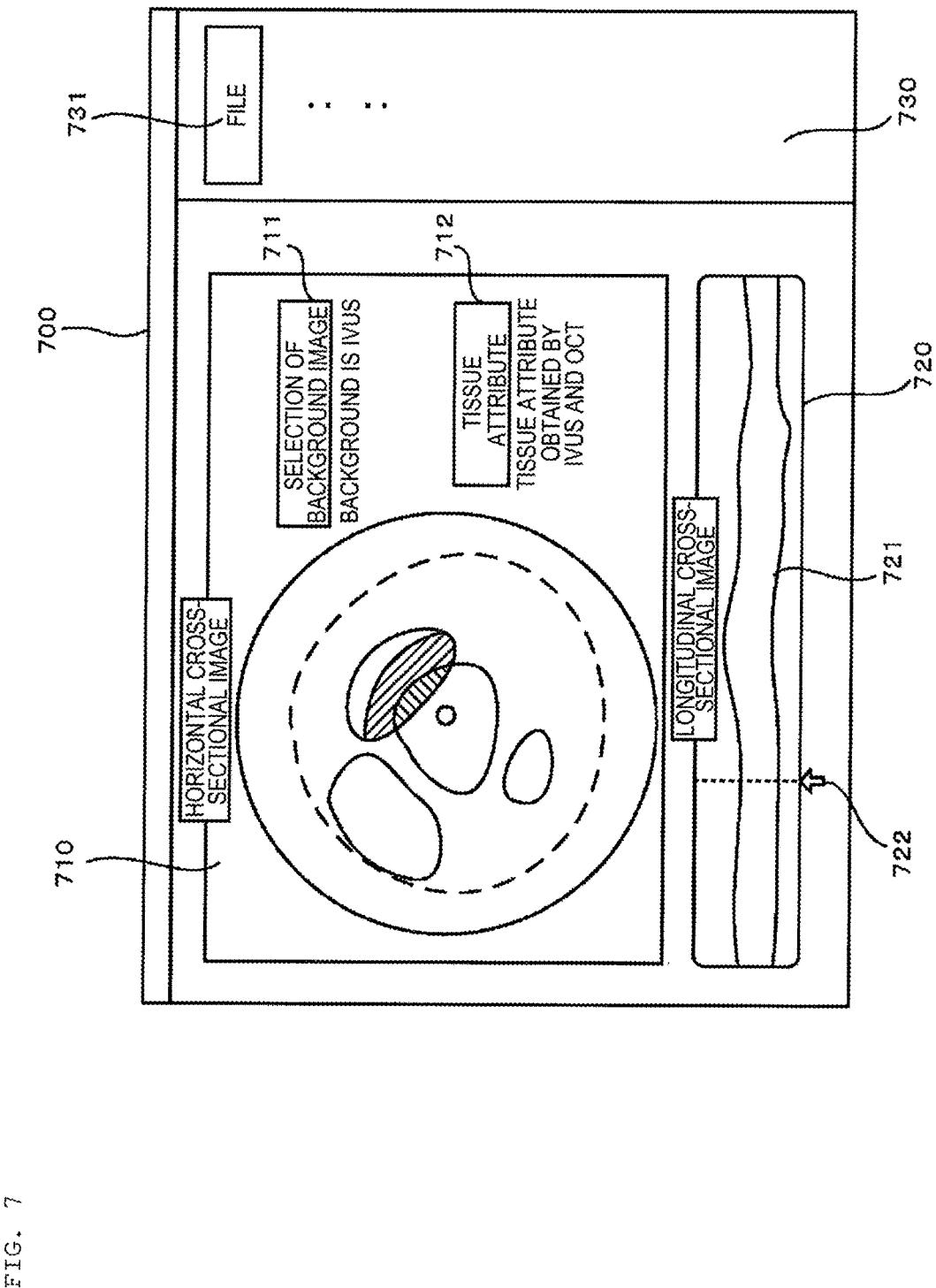
FIG. 7 illustrates an example of a display screen according to the embodiment.

FIG. 7 illustrates a window 700 displayed on a monitor 113 after the imaging apparatus for diagnosis 100 performs a scanning process. The window 700 is roughly divided into display regions 710, 720, and 730.

The display region 710 is a region for displaying a vascular cross-sectional image of a surface orthogonal to the vascular axis. The display region 710 has a button 711 which switches whether to select any image of an ultrasound cross-sectional image, an optical cross-sectional image, and a composite image between the ultrasound cross-sectional image and the optical cross-sectional image as a cross-sectional image to be displayed, and a button 712 which switches whether to display tissue attributes or not, and which switches whether to select the tissue attribute (FIG. 6(c)) obtained from the ultrasound data, the tissue attribute (FIG. 6(b)) obtained from the optical interference data, or the tissue attribute (FIG. 6(d)) applying both items of data, in case where the tissue attributes are displayed. Information indicating what is selected now is displayed in a lower portion of both the buttons.

The display region 720 displays a longitudinal cross-sectional image 721 extending along the vascular axis when scanning is performed. One line portion in the vertical direction of the longitudinal cross-sectional image 721 is configured so that one certain item of optical interference line data stored in the memory 202 and line data obtained by the rotation of 180° therefrom are connected to each other. The horizontal direction of the longitudinal cross-sectional image 721 corresponds to a movement position of the imaging core. According to the embodiment, since a high definition surface is available, the vertical cross-sectional image 721 applies the optical interference line data, but may employ the ultrasound line data. A position of a marker 722 can be moved in the horizontal direction by a user (doctor) operating a mouse 114. A cross-sectional image at a position indicated by the marker 722 is displayed on the display region 710 previously displayed.

The display region 730 has a button arranged therein in order to instruct various processes. If a file button 731 starts to be operated in order to store the line data obtained through scanning or in order to read the data stored in the past, various buttons are arranged. However, the buttons are not included in the essence of the present application, and thus, description thereof will be omitted.

In the above-described window 700, a user can change a position of the marker 722 by operating the mouse 114. If the marker 722 is moved, the signal processing unit 201 causes a vascular cross-sectional image corresponding to the position to be displayed on the display region 710. In this case, any one of the ultrasound cross-sectional image, the optical cross-sectional image, and the composite image between the ultrasound cross-sectional image and the optical cross-sectional image which are designated by the button 711 is displayed. In addition, in this case, in case where an instruction is made so as to display the tissue attributes by using the button 712, the tissue attribute in accordance with the instruction is displayed by being superimposed on the vascular cross-sectional image. If a user operates the button 711 and 712, the user can switch any one of the ultrasound cross-sectional image, the optical cross-sectional image, and the composite image between the ultrasound cross-sectional image and the optical cross-sectional image, as the vascular cross-sectional image to be displayed. As a matter of course, the user can display or not display tissue attribute information, and can designate the tissue attribute when the tissue attribute is displayed.

Figure 8:
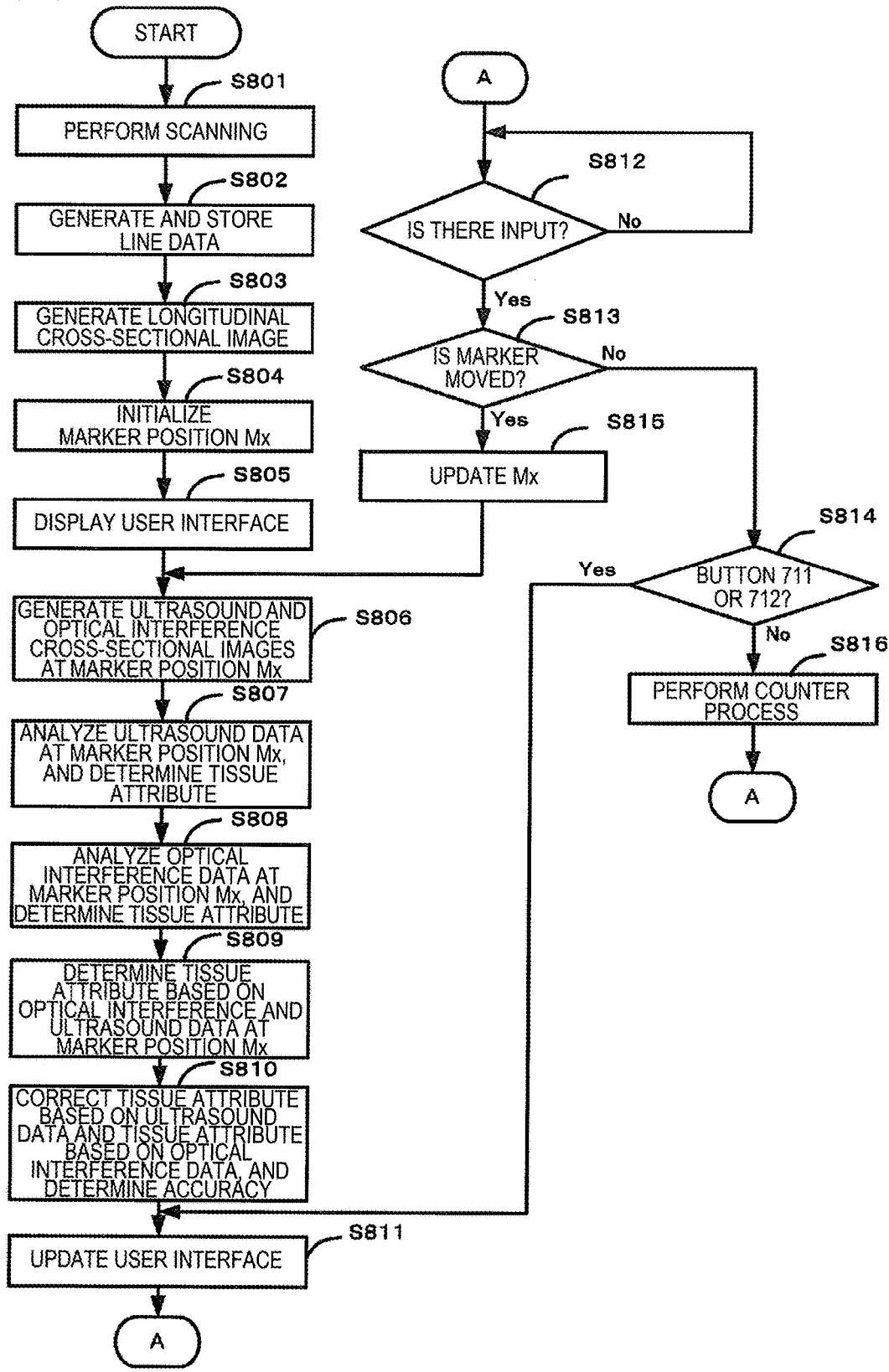
FIG. 8 is a flowchart illustrating a processing procedure in a signal processing unit according to the embodiment.

Lastly, a processing procedure of the signal processing unit 201 according to the embodiment will be described with reference to a flowchart in FIG. 8. A program relating to the drawing is stored in the hard disk 210, is downloaded to the memory 202, and is executed by the signal processing unit 201.

If a user inputs an instruction to perform scanning after inserting a distal end of the probe 101 into a target position in a patient's blood vessel, the signal processing unit 201 controls the pullback unit 102 so as to perform the scanning (Step S801). As a result, the optical interference data and the ultrasound interference data can be obtained from the A/D converters 207 and 235. Accordingly, the signal processing unit 201 temporarily stores both of these in the memory 202. Then, the signal processing unit 201 performs proper processing on these so as to be converted into line data, and causes the memory 202 to store the line data again (Step S802).

Thereafter, the signal processing unit 201 generates a longitudinal vascular cross-sectional image by applying the optical interference line data (Step S803). The longitudinal vascular cross-sectional image may be created by applying the ultrasound line data, and a configuration may be adopted in which a user can select any one of these.

Then, in Step S804, the position of the marker 722 is set to an initial position Mx=0. Then, in Step S805, the signal processing unit 201 causes the monitor 113 to display a window (user interface) illustrated in FIG. 7 which has the longitudinal vascular cross-sectional image at the position of the marker 722.

Thereafter, in Step S806, the signal processing unit 201 generates an ultrasound cross-sectional image and an optical cross-sectional image which correspond to the position Mx of the marker 722. Then, in Step S807, the signal processing unit 201 analyzes the ultrasound data corresponding to the marker position Mx, and performs classification processing on tissue attributes (refer to FIG. 6(a)). In addition, in Step S808, the signal processing unit 201 analyzes the optical interference data corresponding to the marker position Mx, and performs classification processing on tissue attributes (refer to FIG. 6(b)). Furthermore, in Step S809, the signal processing unit 201 performs classification processing on tissue attributes based on both the optical interference data and the ultrasound data. Thereafter, in Step S810, the signal processing unit 201 performs processing for correction or accuracy determination on the tissue attributes, based on the classification result of each tissue attribute. Thereafter, in accordance with a selected state of the buttons 711 and 712, the signal processing unit 201 updates the vascular cross-sectional image and the tissue attribute in the display region 710 on the user interface (Step 811).

As a result of the above-described process, based on the initial value of the marker 722, the window 700 serving as the user interface illustrated in FIG. 7 is displayed. Thereafter, in Step S812, the signal processing unit 201 waits for various instruction input from a user. In case where it is determined that there is the instruction from the user, in Steps S813 and S814, the signal processing unit 201 determines whether the input instruction is an instruction to move the marker 722 or an instruction to operate the buttons 711 and 712. In case where the instruction to move the marker 722 is determined, the signal processing unit 201 updates a variable indicating the marker position Mx in accordance with an instructed position, and performs processes subsequent to Step S806. On the other hand, in case where the instruction is the instruction to operate any one of the buttons 711 and 712, the instruction is not the instruction to change the marker position Mx, and the cross-sectional image and the tissue attribute which are to be displayed have already been built. Accordingly, the processes subsequent to Step S811 are performed. In addition, in case where it is determined that the instruction is not the instruction to move the marker 722 or the instruction to operate the buttons 711 and 712, the corresponding process is performed in Step S816.

As described above, according to the present embodiment, the vascular tissue attributes are classified, based on both the ultrasound data and the optical interference data. Therefore, it is possible to estimate whether the tissue attributes are accurate or inaccurate. Furthermore, it is also possible to estimate the tissue attributes which cannot be estimated by single scanning data used so far.

In addition, as is understood from the above-described embodiment, the processes according to the embodiment are mostly performed by the signal processing unit 201 configured to include a microprocessor. Accordingly, a program causes the microprocessor to execute the processes in order to realize the function. Therefore, as a matter of course, the program is also included in the scope of the present invention. In addition, the program is normally stored in a tangible, non-transitory computer-readable recording medium such as a CD-ROM, a DVD-ROM. The program can cause the microprocessor to execute the processes by the program being set in a reading device (CD-ROM drive or the like) belonging to a computer and being copied to or installed in a system. Therefore, it is apparent that the related computer-readable recording medium is also included in the scope of the present invention.

The detailed description above describes a diagnostic imaging apparatus, control method, program, and computer-readable storage medium. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. An imaging apparatus for diagnosis which generates a vascular cross-sectional image based on ultrasound and a vascular cross-sectional image based on optical interference, comprising:
    a probe for rotatably and movably accommodating an imaging core having an ultrasound transceiver and an optical transceiver;
    a processor configured to: 1) classify distribution and a type of tissue attribute in a vascular cross section, based on reflected wave data of ultrasound detected by the imaging core; 2) classify the distribution and the type of the tissue attribute in the vascular cross section, based on interference light data including a reflected wave of light detected by the imaging core; 3) determine a match or mismatch of classification of the type of tissue attribute of a corresponding portion, as classified based on the reflected wave data of ultrasound detected by the imaging core, and as classified based on the interference light data including the reflected wave of light detected by the imaging core, and 4) determine the type of tissue attribute, with an accuracy grade, at the corresponding portion based on the determined match or mismatch of classification and a predetermined database; and
    display means for displaying the distribution of tissue attributes determined by the processor in a display form in which the match or mismatch can be identified.

2. The imaging apparatus for diagnosis according to claim 1,
    wherein the display means displays the distribution of the body tissue attributes determined by the determination means processor by superimposing the distribution on any background image of an ultrasound cross-sectional image, an optical interference cross-sectional image, and a composite image between an ultrasound cross-sectional image and an optical interference cross-sectional image, in the display form in which the match or mismatch can be identified.

3. The imaging apparatus for diagnosis according to claim 2, further comprising:
    first selection means for selecting any one of the ultrasound cross-sectional image, the optical interference cross-sectional image, and the composite image between the ultrasound image and the optical tomographic image, as the background image displayed by the display means.

4. The imaging apparatus for diagnosis according to claim 1, further comprising:
selection means for selecting any one for display, as the tissue attributes displayed by the display means, among the tissue attributes obtained from reflected wave data of ultrasound, the tissue attributes obtained from interference light data, and tissue attribute information based on both the ultrasound reflected wave data and the interference light data.

5. The imaging apparatus for diagnosis according to claim 2, further comprising:
selection means for selecting any one for display, as the tissue attributes displayed by the display means, among the tissue attributes obtained from reflected wave data of ultrasound, the tissue attributes obtained from interference light data, and tissue attribute information based on both the ultrasound reflected wave data and the interference light data.

6. The imaging apparatus for diagnosis according to claim 3, further comprising:
second selection means for selecting any one for display, as the tissue attributes displayed by the display means, among the tissue attributes obtained from reflected wave data of ultrasound, the tissue attributes obtained from interference light data, and tissue attribute information based on both the ultrasound reflected wave data and the interference light data.

7. An imaging apparatus for diagnosis which generates a vascular cross-sectional image based on ultrasound and a vascular cross-sectional image based on optical interference, comprising:
a probe for rotatably and movably accommodating an imaging core having an ultrasound transceiver and an optical transceiver;
a processor configured to: 1) classify distribution and a type of tissue attribute in a vascular cross section, based on reflected wave data of ultrasound detected by the imaging core; 2) classify the distribution and the type of the tissue attribute in the vascular cross section, based on interference light data including a reflected wave of light detected by the imaging core; 3) determine a match or mismatch of classification of the type of tissue attribute of a corresponding portion, as classified based on the reflected wave data of ultrasound detected by the imaging core, and as classified based on the interference light data including the reflected wave of light detected by the imaging core, and 4) determine the type of tissue attribute at the corresponding portion, with an accuracy grade, based on the determined match or mismatch of classification and a predetermined database; and
display means for displaying the type of the tissue attribute determined at the corresponding portion, with the accuracy grade, based on the determined match or mismatch of classification and the predetermined database.

8. The imaging apparatus for diagnosis according to claim 7, further comprising:
selection means for selecting any one for display, as the tissue attributes displayed by the display means, among the tissue attributes obtained from reflected wave data of ultrasound, the tissue attributes obtained from interference light data, and tissue attribute information based on both the ultrasound reflected wave data and the interference light data.

9. A control method of an imaging apparatus for diagnosis which generates a vascular cross-sectional image based on ultrasound and a vascular cross-sectional image based on optical interference by using a probe for rotatably and movably accommodating an imaging core having an ultrasound transceiver and an optical transceiver, the method comprising:
a first classification process of classifying distribution and a type of tissue attribute in a vascular cross section, based on reflected wave data of ultrasound detected by the imaging core;
a second classification process of classifying the distribution and the type of the tissue attribute in the vascular cross section, based on interference light data including a reflected wave of light detected by the imaging core;
a determination process of determining a match or mismatch of classification of the type of tissue attribute of a corresponding portion, as classified based on the reflected wave data of ultrasound detected by the imaging core, and as classified based on the interference light data including the reflected wave of light detected by the imaging core, and determining the type of tissue attribute, with an accuracy grade, at the corresponding portion based on the determined match or mismatch of classification and a predetermined database; and
a display control process, wherein the display control process comprises one or more of displaying the distribution of tissue attributes determined by the determination process in a display form in which the match or mismatch can be identified or displaying the type of the tissue attribute determined at the corresponding portion, with the accuracy grade, based on the determined match or mismatch of classification and the predetermined database.

* * * * *